(12) United States Patent
Jung et al.

(10) Patent No.: US 8,326,645 B2
(45) Date of Patent: *Dec. 4, 2012

(54) VERIFICATION TECHNIQUE FOR PATIENT DIAGNOSIS AND TREATMENT

(75) Inventors: Edward K. Y. Jung, Bellevue, WA (US); Royce A. Levien, Lexington, MA (US); Robert W. Lord, Seattle, WA (US); Mark A. Malamud, Seattle, WA (US); John D. Rinaldo, Jr., Bellevue, WA (US); Lowell L. Wood, Jr., Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1224 days.

This patent is subject to a terminal disclaimer.

(21) Appl. No.: 11/580,692

(22) Filed: Oct. 12, 2006

(65) Prior Publication Data

US 2008/0000994 A1 Jan. 3, 2008

Related U.S. Application Data

(63) Continuation-in-part of application No. 11/489,244, filed on Jul. 18, 2006, and a continuation-in-part of application No. 11/478,569, filed on Jun. 29, 2006.

(51) Int. Cl.
*G06F 19/00* (2006.01)
*G06Q 10/00* (2006.01)
(52) U.S. Cl. .............................. 705/2; 705/3
(58) Field of Classification Search .............. 705/2, 3, 705/4
See application file for complete search history.

(56) References Cited

U.S. PATENT DOCUMENTS

| | | | |
|---|---|---|---|
| 3,970,996 | A | 7/1976 | Yasaka et al. |
| 4,156,620 | A | 5/1979 | Clemens |
| 4,164,320 | A | 8/1979 | Irazoqui et al. |
| 4,695,954 | A | 9/1987 | Rose et al. |
| 4,781,704 | A | 11/1988 | Potter |
| 4,843,377 | A | 6/1989 | Fuller et al. |
| 4,857,713 | A | 8/1989 | Brown |
| 4,857,716 | A | 8/1989 | Gombrich et al. |
| 4,930,997 | A | 6/1990 | Bennett |
| 4,999,613 | A | 3/1991 | Williamson et al. |
| 5,026,084 | A | 6/1991 | Pasfield |
| 5,092,850 | A | 3/1992 | Buma |
| 5,947,937 | A | 9/1999 | Urrutia et al. |
| 6,024,699 | A | 2/2000 | Surwit et al. |
| 6,294,999 | B1 | 9/2001 | Yarin et al. |
| 6,380,858 | B1 | 4/2002 | Yarin et al. |
| 6,454,705 | B1 | 9/2002 | Cosentino et al. |
| 6,523,009 | B1 | 2/2003 | Wilkins |
| 6,575,969 | B1 | 6/2003 | Rittman, III et al. |
| 6,671,563 | B1 | 12/2003 | Engelson et al. |

(Continued)

OTHER PUBLICATIONS

"Acquiring, Organizing, and Displaying Medical Information"; *Insight*: A Tool for Viewing Data, Finding Answers, and Seeing Patterns; bearing a date of 2006; pp. 1-7.

(Continued)

*Primary Examiner* — Robert Morgan
*Assistant Examiner* — Sean K Hunter

(57) ABSTRACT

Exemplary embodiments provide a verification technique that facilitates administration of a health-related procedure to an intended recipient patient or group of patients. An interface template may be configured to establish verifiable matching engagement between the patient and various types of objects used to administer the health-related procedure.

25 Claims, 9 Drawing Sheets

U.S. PATENT DOCUMENTS

| | | |
|---|---|---|
| 6,699,193 B2 | 3/2004 | Crutchfield et al. |
| 6,790,198 B1 | 9/2004 | White et al. |
| 6,824,052 B2 | 11/2004 | Walsh |
| 6,980,111 B2 | 12/2005 | Nolte |
| 7,029,034 B2 | 4/2006 | Newell |
| 7,039,628 B2 | 5/2006 | Logan, Jr. |
| 7,321,862 B2 | 1/2008 | Rosenfeld et al. |
| 7,411,509 B2 | 8/2008 | Rosenfeld et al. |
| 7,853,455 B2 | 12/2010 | Brown |
| 2001/0054155 A1 | 12/2001 | Hagan et al. |
| 2002/0016719 A1 | 2/2002 | Nemeth et al. |
| 2002/0022972 A1 | 2/2002 | Costello |
| 2002/0032583 A1 | 3/2002 | Joao |
| 2002/0052763 A1* | 5/2002 | Jung Richardson ............... 705/3 |
| 2002/0055858 A1 | 5/2002 | Jackson |
| 2002/0065686 A1 | 5/2002 | Monteleone et al. |
| 2002/0067270 A1 | 6/2002 | Yarin et al. |
| 2002/0188259 A1 | 12/2002 | Hickle et al. |
| 2003/0022141 A1 | 1/2003 | Packard |
| 2003/0036683 A1 | 2/2003 | Kehr et al. |
| 2003/0040700 A1 | 2/2003 | Hickle et al. |
| 2003/0140928 A1 | 7/2003 | Bui et al. |
| 2003/0208382 A1 | 11/2003 | Westfall |
| 2003/0212579 A1 | 11/2003 | Brown et al. |
| 2004/0010425 A1 | 1/2004 | Wilkes et al. |
| 2004/0026501 A1 | 2/2004 | Walsh |
| 2004/0045031 A1 | 3/2004 | Gautier |
| 2004/0203692 A1 | 10/2004 | Schwinke et al. |
| 2004/0254816 A1 | 12/2004 | Myers |
| 2005/0060188 A1 | 3/2005 | Valley |
| 2005/0119534 A1 | 6/2005 | Trost et al. |
| 2005/0139651 A1* | 6/2005 | Lim et al. ...................... 235/380 |
| 2005/0165627 A1 | 7/2005 | Fotsch et al. |
| 2005/0187789 A1 | 8/2005 | Hatlestad et al. |
| 2005/0218152 A1 | 10/2005 | Simon |
| 2005/0240304 A1 | 10/2005 | York et al. |
| 2005/0251102 A1 | 11/2005 | Hegland et al. |
| 2005/0258244 A1 | 11/2005 | Mitchell et al. |
| 2006/0028727 A1 | 2/2006 | Moon et al. |
| 2006/0058917 A1 | 3/2006 | Vonk et al. |
| 2006/0061472 A1 | 3/2006 | Lovoi et al. |
| 2006/0064087 A1 | 3/2006 | Mirza et al. |
| 2006/0097516 A1 | 5/2006 | Kozlowski et al. |
| 2006/0229918 A1 | 10/2006 | Fotsch et al. |
| 2006/0265245 A1 | 11/2006 | McCallie et al. |
| 2007/0016443 A1 | 1/2007 | Wachman et al. |
| 2007/0018121 A1 | 1/2007 | Leyman et al. |
| 2007/0043590 A1 | 2/2007 | Lee |
| 2007/0061167 A1 | 3/2007 | Brown |
| 2007/0233854 A1 | 10/2007 | Bukovec et al. |
| 2007/0274574 A1 | 11/2007 | Boult et al. |

OTHER PUBLICATIONS

Aller, MD, Raymond; "Positive patient identification: more than a double check"; System Review Series; bearing a date of Oct. 2005; pp. 26-34.

Avery, Catherine; "Quantum Leap in Medical Infomatics"; Washington Hospital Center Physician; vol. 10—No. 10; bearing a date of Dec. 2004-Jan. 2005; pp. 1, 10-11.

Beyea, Suzanne C.; "Patient identification—a crucial aspect of patient safety—Patient Safety First"; AORN Journal; bearing a date of Sep. 2003; pp. 1-3.

Beyea, Suzanne C.; "Systems that reduce the potential for patient identification errors"; AORN Journal; bearing a date of Sep. 2002; pp. 1-4.

"Convergence CT Introduces Inpatient Insight Hospital Patient-Level Data for Pharmaceutical Market Research and Clinical Trial Planning;" San Francisco—(Business Wire)—Nov. 13, 2003; pp. 1; located at http://findarticles.com/p/articles/mi_m0EIN/is_2003_Nov_13/ai_n27 . . . .

"Former head of UHP's DUI unit ends appeal of alcohol-related conviction"; The Salt Lake Tribune; bearing a date of Mar. 3, 2008; pp. 1-2; located at http://www.sltrib.com/fdcp?1204574945509.

Greene, Jay; "COVER STORY Essential news and information for physician business executives"; vol. 10/No. 10; bearing a date of Oct. 2006; pp. 1-7.

Holstein, William J.; "Patient Safety Through Technology"; Published Feb. 17, 2007, The New York Times; pp. 1-2.

McCarthy, Caroline; "Microsoft coughs up for health care software"; c/net news.com; bearing a date of Jul. 27, 2006; pp. 1-2; located at http://news.com.com/2102-1014_3-6098696.html?tag=st.util.print.

Microsoft Executive Circle Case Study Detail; "Washington Hospital Center"; bearing a date of Jan. 20, 2004; pp. 1-5; located at http://www.microsoft.com/business/executivecircle/content/casestud . . . .

"PAR3 and Vitality, Inc. Join Forces to Improve Medication Adherence With Combined Solutions"; PAR3 Communications, Inc.; bearing a date of Aug. 28, 2007; pp. 1-2; located at http://www.prnewswire.ca/cgi-bin/stories.pl?ACCT=104&STORY . . . .

"Precision Dynamics' Bar Code System Solutions for Positive Patient Identification Featured at MUSE Conference"; Precision Dynamics Corporation; bearing a date of May 4, 2006; pp. 1-2.

Symbol Technologies, Inc.; "Safer Patient Care: Automated Medication Verification Solutions for Hospitals and Clinics"; bearing a date of 2003; pp. 1-3.

The Whittington Hospital NHS Trust; "Information for Staff to Accompany Patient Identification Policy"; bearing a date of Mar. 2003; pp. 1-14.

Versweyveld, Leslie; "Misys Insight clinical decision support tool integrates data from heterogeneous, enterprise-wide health care systems"; Virtual Medical Worlds Monthly; bearing a date of Jul. 23, 2002; pp. 1-3; located at http://www.hoise.com/vmw/02/articles/vmw/LV-VM-08-02-15.html.

White, Charlie; "Glowcap Ambient Pill Cap"; Bearing a date of May 29, 2007; pp. 1.

Pending U.S. Appl. No. 11/149,964, Jung et al.

* cited by examiner

VERIFICATION TECHNIQUE FOR PATIENT DIAGNOSIS AND TREATMENT

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

Related Applications

For purposes of the USPTO extra-statutory requirements, the present application constitutes a continuation-in-part of U.S. patent application Ser. No. 11/478,569 entitled VERIFICATION TECHNIQUE FOR PATIENT DIAGNOSIS AND TREATMENT, naming Edward K. Y. Jung, Royce A. Levien, Robert W. Lord, Mark A. Malamud, John D. Rinaldo, Jr. and Lowell L. Wood, Jr. as inventors, filed 29 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/489,244 entitled ENHANCED COMMUNICATION LINK FOR PATIENT DIAGNOSIS AND TREATMENT, naming Edward K. Y. Jung, Royce A. Levien, Robert W. Lord, Mark A. Malamud, John D. Rinaldo, Jr. and Lowell L. Wood, Jr. as inventors, filed 18 Jul. 2006, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at ttp://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BACKGROUND

Systems and methods for providing diagnosis, treatment, and other health-related procedures need additional safeguards to help assure proper administration to a designated patient.

SUMMARY

Various embodiments and implementations are disclosed herein with respect to improved systems and methods for administering appropriate health-related procedures to one or more patients.

Some system embodiments for patient verification may include a primary version of an interface template that serves as an identifier for a health-related issue involving a particular patient; a secondary version of the interface template that is associated with a selected procedure intended for the particular patient; and a customized interface configuration that is incorporated on both the primary version and the secondary version of the interface template, which interface configuration is shaped for matching engagement to assure administration of the selected procedure to the particular patient.

Other system embodiments for a patient identification system may include a health-related procedure that is intended to be rendered to a particular patient; one or more product components to be used in connection with said health-related procedure; and an interface template associated with the particular patient, which interface template includes a customized interface configuration shaped for verifiable matching engagement with a complementary interface template associated with the health-related procedure.

Additional system embodiments for a patient identification system may include a health-related procedure that is intended to be rendered to one or more patients; one or more product components to be used in connection with said health-related procedure; and an interface template that includes a customized configuration associated with the one or more product components, wherein the customized interface configuration includes a shaped pattern for verifiable matching engagement with a complementary interface template associated with the one or more patients.

An exemplary process embodiment for patient verification may include establishing an interface template to serve as an identifier for a health-related issue involving a particular patient, adopting a primary version of the interface template that is located in proximity to the particular patient, adopting a secondary version of the interface template that is shaped for verifiable matching engagement with the primary version of the interface template, and associating the secondary version of the interface template with a selected procedure intended for the particular patient.

Various process components may be incorporated in computer program products having instructions encoded on storage or transmission media for executing and implementing the process steps.

Another exemplary embodiment may provide a patient identification system that includes a health-related procedure that is intended to be rendered to a specified group of patients having a same or similar type of health-related issue; one or more product components to be used in connection with said health-related procedure; and an interface template associated with the one or more product components, which interface template includes a customized interface configuration shaped for verifiable matching engagement with a complementary interface template associated with one or more of the patients in the specified group.

A further possible system embodiment for patient identification may include an interface template associated with the particular patient, which interface template includes a customized interface configuration shaped for verifiable matching engagement with a complementary interface template associated with a health-related procedure to be rendered to the particular patient.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
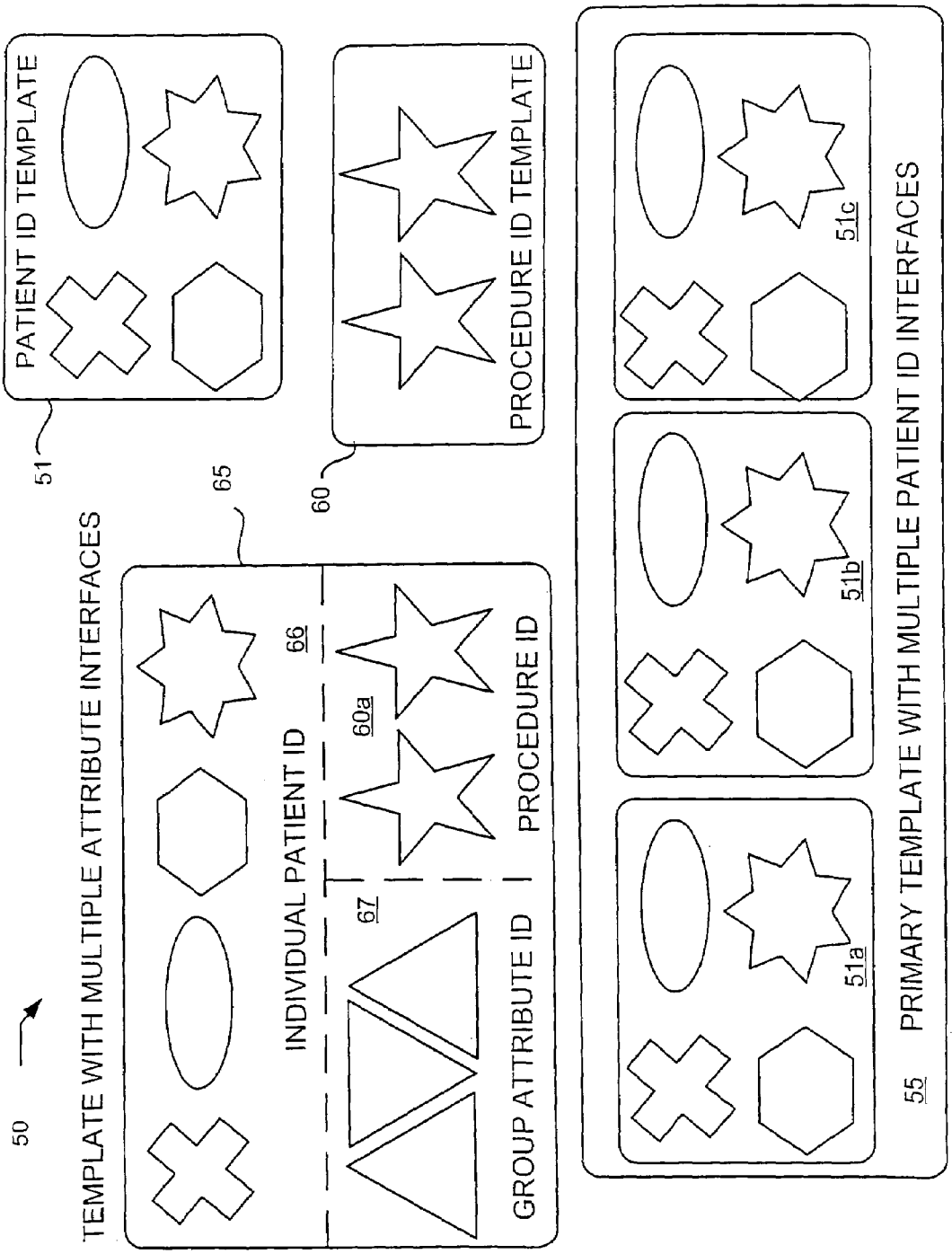
FIG. 1 is a schematic representation of exemplary patient verification features that may be incorporated in an interface template.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The patient identification techniques disclosed herein may be adapted for the administration of many types of health-related procedures. Accordingly it is not possible to recite a complete listing of such health-related procedures that may incorporate the various interface template aspects illustrated in the exemplary disclosed embodiments.

However it may be helpful to understand a recently developed technique for marking medication and other health-related products with a visual identifier that facilitates proper administration of a substance dosage to designated patent. In that regard the following commonly assigned pending application is incorporated herein by reference: Ser. No. 11/474,109 entitled "Customized Visual Marking for Medication Labeling", filed 23 Jun. 2006.

It will be further understood that patient identification issues involving administration of health-related procedures affect many types of persons and entities including but not limited to manufacturers, distributors, wholesalers, retailers, hospitals, hospices, convalescent homes, emergency care facilities, pharmacies, health insurance providers, HMOs, clinics, home nursing services, and the like. It is believed that the various aspects and implementations for the patient verification techniques disclosed herein can be adapted for the benefit of such persons and entities as well as for the benefit of their clients and patients.

The exemplary patient verification features 50 shown in FIG. 1 include a patient ID template 51, a primary template 55 with multiple patient ID interfaces, and another template 65 with multiple attribute interfaces. It will be understood that an exemplary template associated with a particular patient may be configured as an interface for verifiable matching engagement with secondary template associated with a health-related procedure.

The patient ID template 51 includes various interface elements (e.g., shown schematically as a four-part configuration) that collectively serve as an identifier for health-related issues involving a particular patient, or in some instances a group of patients. Such a patient interface configuration may be implemented in a primary version of an interface template associated with a particular patient (e.g., attached to a body part, attached to a patient identifier, located proximate to a patient, incorporated with a patient support structure, located remotely from the patient, etc.), and also implemented in a complementary secondary version of the interface template that may be associated with a selected procedure intended for the particular patient or group of patients.

The primary template 55 shows an exemplary implementation of a composite three interface template that may be located in proximity to the particular patient. It will be noted that such a unitary interface template may have practical advantages as compared to using three separate patient ID templates 51. However it will be noted that multiple unitary templates as well as a composite multiple interface template allow for possible simultaneous matching engagement with three different selected patient procedures, and also for matching engagement with secondary procedure ID templates associated with different components of a health-related procedure.

The procedure ID template 60 includes various interface elements (e.g., shown schematically as a twin-type configuration) that collectively serve as an identifier for health-related issues involving a specified type of patient procedure.

The template 65 is shown schematically with an individual patient ID interface 66, a procedure ID interface 60a, and a group attribute ID interface 67. The individual patient ID interface 66 includes a different layout of the four-part configuration shown in patient ID template 51, but both interface configurations 51, 66 may serve as an identifier for the same particular patient. It will be noted that the procedure ID interface 60a incorporates the same twin-type configuration as shown in procedure ID template 60 in order for both interface configurations of 60, 60a to serve as an identifier for the same health-related procedure.

The triplet-type interface configuration shown in group attribute ID 67 provides capability for a template configuration to serve as an identifier of several patients that share a health-related relationship or affiliation.

It will be understood from the illustrated embodiments disclosed herein that some implementations may provide a patient identifier attachable to a bodily part of the particular patient, which patient identifier includes or is physically coupled to the interface template. In some instances the patient identifier may be attachable to a support structure for the particular patient, which patient identifier includes or is physically coupled to the interface template.

Further possible embodiments may provide an interface template in proximity to the particular patient, or provide an interface template located remotely from the particular patient. Other possible implementations may provide a plurality of interface templates including a first attribute interface serving as an identifier of the particular patient and a second attribute interface serving as an identifier of the health-related procedure. Such interface templates may be complementary to matching interface template configurations associated with a particular health-related procedure.

Some embodiments may provide a plurality of complementary interface templates that include a first attribute interface serving as an identifier of the particular patient and a second attribute interface serving as an identifier of a group of patients having a same or similar type of health-related issue. Other possible system features may include a plurality of complementary interface templates having two or more attribute interfaces each serving as an identifier of the particular patient to enable verifiable matching engagement with multiple complementary interface templates associated with a health-related procedure.

Some embodiments may further provide a computer program product including instructions encoded on storage or transmission media, which instructions implement a process for verification of the matching engagement between the interface template associated with the particular patient and the complementary interface template associated with a health-related procedure to be rendered to the particular patient.

Additional embodiments may provide a computer program product including instructions encoded on storage or transmission media, which instructions implement a process for providing a status indication regarding whether the matching engagement has occurred between the interface template associated with the particular patient and the complementary interface template associated with a health-related procedure to be rendered to the particular patient.

Further possible embodiments may provide a computer program product including instructions encoded on storage or transmission media, which instructions implement a process for preventing activation of the health-related procedure in the absence of satisfactory matching engagement between the interface template associated with the particular patient and the complementary interface template associated with a health-related procedure to be rendered to the particular patient.

Figure 2:
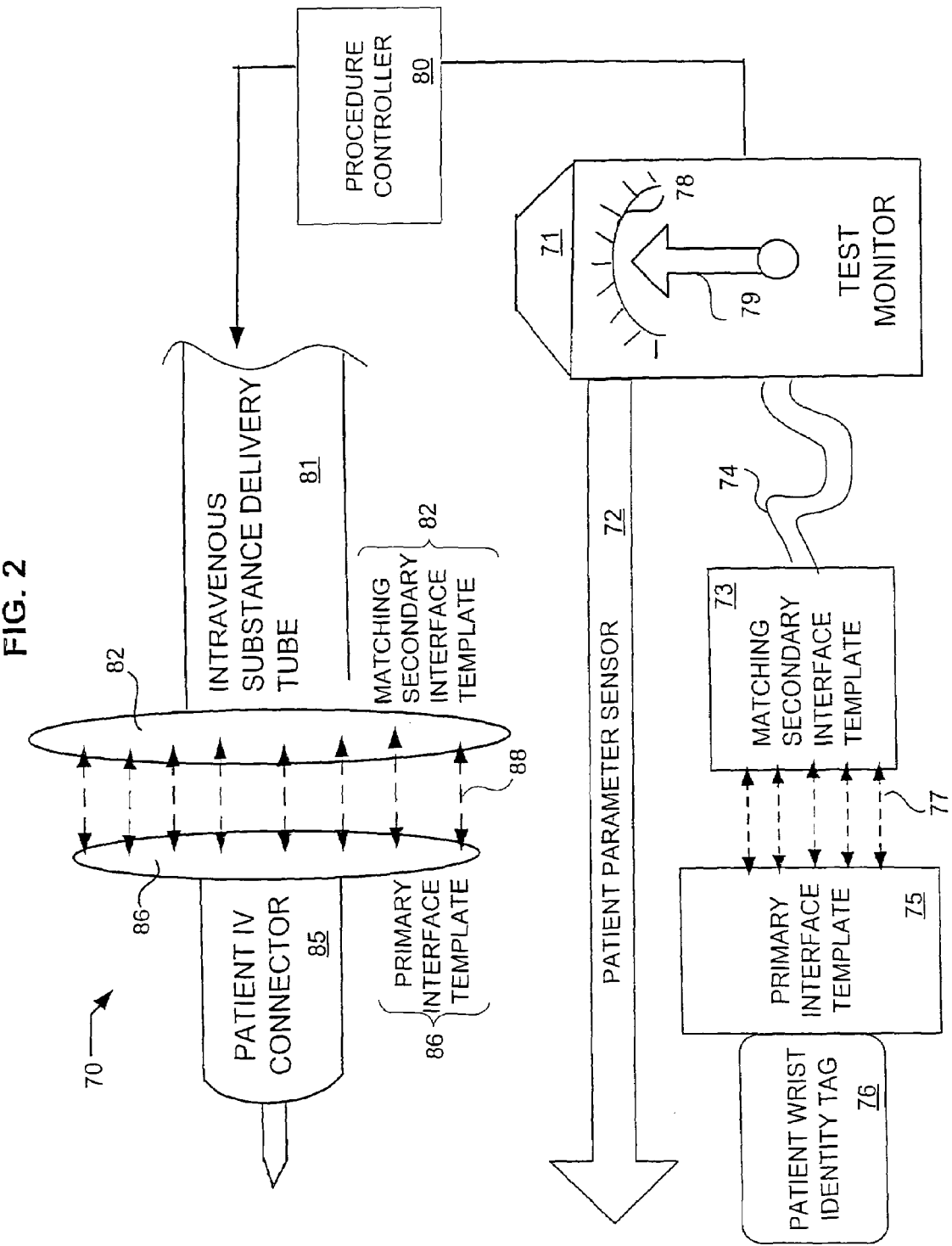
FIG. 2 is a schematic representation of exemplary embodiments that may be implemented in connection with a health-related procedure

The exemplary embodiments 70 of FIG. 2 disclose test monitor 71, patient parameter sensor 72, connector link 74, and procedure controller 80 operably coupled with intravenous substance delivery tube 81. A designated patient who is an intended recipient of the intravenous administration procedures may have a patient wrist identity tag 76 integral with or attachable to a primary interface template 75, and may also have a patient IV connector 85 integral with or attachable to primary interface template 86. The delivery of a health-related substance dosage to the designated patient via the intravenous substance delivery tube 81 may be coordinated by procedure controller 80 with output results generated by test monitor 71. The test monitor 71 may include an indicator arrow 79 that moves along a readout scale 78 to indicate an output result received from the patient parameter sensor 72.

The primary interface templates 75, 86 directly associated with the designated patient may be incorporated in a composite unit (e.g., see primary template 55 in FIG. 1), or may be incorporated in separate units (e.g., see patient ID template 51 in FIG. 1).

It will be noted that an implementation feature of the exemplary embodiments 70 includes a provision for both intravenous procedure components 71, 81 to have separate patient verification interconnections, respectively. Verification for usage of the test monitor 71 with the designated patient is accomplished by correlated interface engagement 77 between primary interface template 75 and matching secondary interface template 73. Verification for usage of the intravenous substance delivery tube 81 with such designated patient is accomplished by correlated interface engagement 88 between primary interface template 86 and matching secondary interface template 82.

Of course it will be understood that in some circumstances a health-related procedure may be configured to have a single patient verification interconnection linked to two or more components used to administer the procedure. In that regard the exemplary embodiments disclosed herein are for purposes of illustration only and are not intended to be limiting.

A substance administration device may be used in connection with administration of the selected procedure, wherein the secondary version of the interface template is associated with the substance administration device.

It will be understood from the various disclosures herein that an exemplary system embodiment may provide the secondary version of the interface template as an integral part of the substance administration device. A further implementation feature may provide a separate product component not integral with the substance administration device, wherein the separate product component includes the secondary version of the interface template as an integral part.

Some embodiments may include a status indicator that is operably coupled to the primary version or said secondary version of the interface template, wherein the status indicator confirms the satisfactory matching engagement between the primary and secondary versions of the interface template. A further system feature may include a control module operably coupled with the substance administration device to prevent activation of the substance administration device in the event there is no verifiable matching engagement between said primary and secondary versions of the interface template. In some instances the control module may be operably coupled with the substance administration device to allow activation of the substance administration device in the event there is confirmation of matching engagement between the primary and secondary versions of the interface template.

It will be understood that various features disclosed herein may be implemented with a diagnostic or testing or treatment device used in connection with administration of the selected health-related procedure, wherein the secondary version of the interface template is associated with such diagnostic or testing or treatment device.

Another exemplary implementation embodiment may include a health-related procedure that involves multiple components which may individually or collectively be integrated with or associated with the secondary version of the interface template.

Further exemplary implementations embodiments may include a patient identification system involving a health-related procedure for administering or dispensing substance dosages of various medications, dietary supplements, test fluids, anesthetics, treatment remedies, etc. (a complete listing is not reasonably possible). The related components used with such a procedure may be integrated with or associated with a complementary secondary version of the interface template.

Other implementations may provide a patient data record used in connection with administration of the selected health-related procedure, wherein the secondary version of the interface template is associated with the patient data record. In some instances a control module may include an access protocol to prevent read access to the patient data record in the event there is no verifiable matching engagement between said primary and secondary versions of the interface template. A further possible system feature may provide a control module that includes an access protocol to prevent write access to the patient data record in the event there is no verifiable matching engagement between said primary and secondary versions of the interface template.

Other possible data record aspects may include a control module having an access protocol to allow read access to the patient data record in the event there is confirmation of matching engagement between said primary and secondary versions of the interface template. Such access protocol may include one or more of the following type of output read access to the patient data record: hardcopy view, hardcopy printout, display monitor, remote access, text access, audio access, image access, fax access, hyperlinked access, and cross-reference link.

Another possible data record aspect may include a control module having an access protocol to allow write access to the patient data record in the event there is confirmation of matching engagement between said primary and secondary versions of the interface template. Such access protocol may allow one or more of the following type of input write access to the patient data record in the event there is confirmation of matching engagement between said primary and secondary versions of the interface template: handwritten, keyboarded, scanned, oral, faxed, remote transmittal, wireless transmittal, data modification, data deletion, hyperlinked data entry, and cross-reference link.

Figure 3:
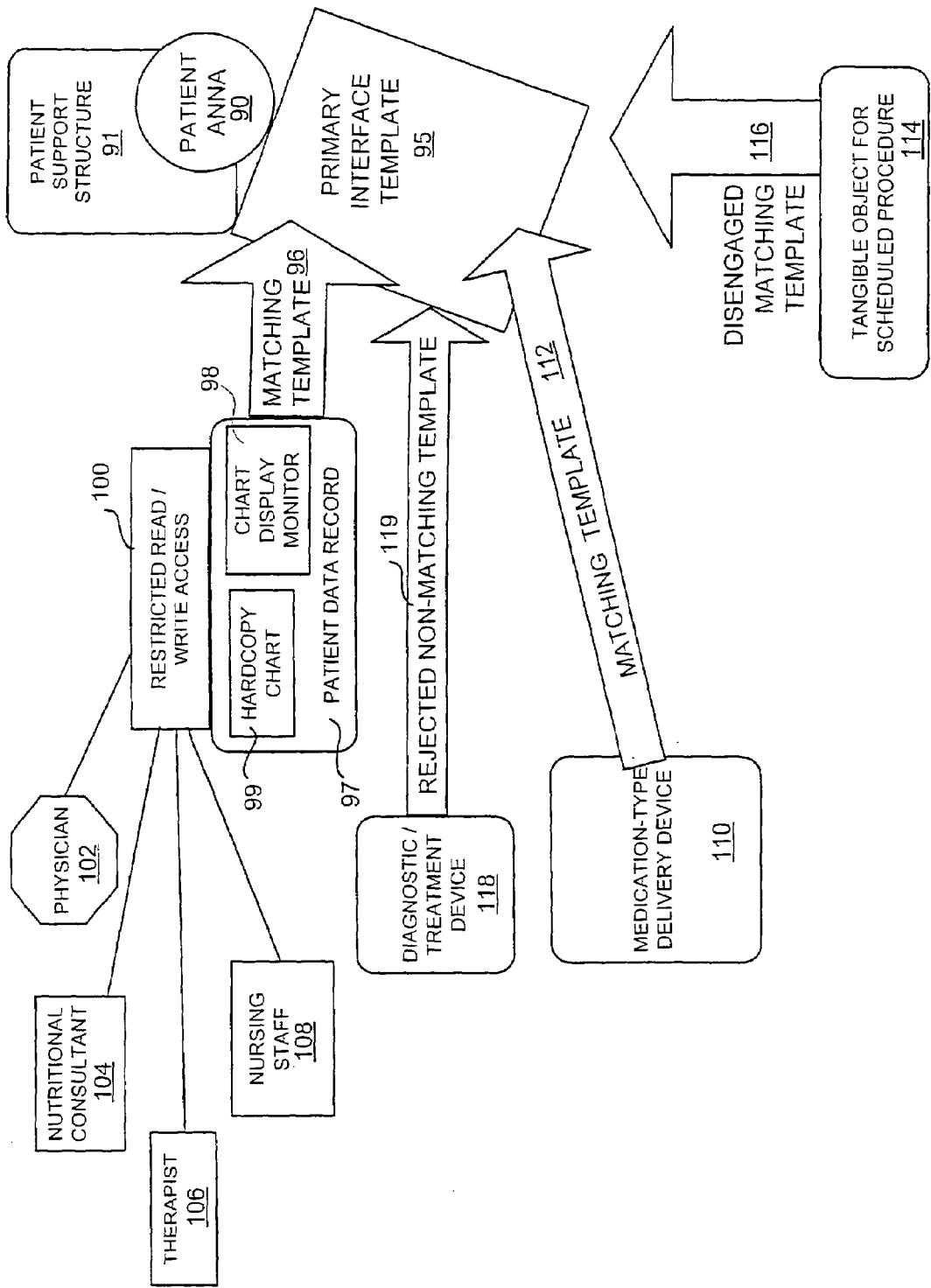
FIG. 3 is a schematic system diagram that illustrates various exemplary patient verification features.

Referring to the exemplary embodiments of FIG. 3, a patient Anna 90 may be temporarily or semi-permanently located with a patient support structure 91 (e.g., chair, bed, gurney, operating table, etc.). One or more primary interface templates 95 may be situated in proximity with patient Anna and/or in close proximity with her patient support structure 91.

It will be understood that health-related procedures can be administered to patient Anna 90 during confinement at a temporary care facility as well as during her daily life activities at a residence, home, work location, or traveling from one place to another. In that regard the exemplary patient verification arrangements disclosed herein are adaptable for use in many different types of patient environments.

An exemplary health-related procedure may include maintenance of a patient data record 97 that may be accessible to patient Anna 90 as well as to other authorized parties such as physician 102, nutritional consultant 104, therapist 106, and nursing staff 108. In order to help assure an acceptable assurance of data integrity, the patient data record 97 may include a restricted read/write access module 100. In some instances a verifiable engagement between Anna's primary interface template 95 and a matching template 96 associated with Anna's patient data record 97 may be required in order before allowing any "read" access (e.g., using hardcopy chart 99 or chart display monitor 98, etc.) or before allowing any "write" access (e.g., handwritten entry, keyboarded entry, scanned entry, etc.) to such patient data record 97.

An exemplary illustrated depiction in FIG. 3 shows the matching template 96 successfully linked together with primary interface template 95 based on a correlated interface engagement.

Other exemplary health-related procedures disclosed in the embodiments of FIG. 3 may involve the use of a medication-type delivery device 110, a tangible object for scheduled procedure 114, and a diagnostic/treatment device 118. Of course it will be understood that many other health-related procedures may also incorporate the patient verification techniques and features disclosed herein.

A further exemplary illustrated depiction in FIG. 3 shows the matching template 112 associated with medication-type deliver device 110 successfully linked together with primary interface template 95 based on a correlated interface engagement. It is noted that successful linkage involving primary patient interface templates may in some instances occur concurrently with multiple secondary interface templates (e.g., see templates 96, 112) associated with different health-related procedures.

Another exemplary illustrated depiction in FIG. 3 shows disengaged matching template 116 associated with tangible object for scheduled procedure 114 awaiting successful linkage with primary interface template 95.

An additional illustrated depiction in FIG. 3 shows an unsuccessful link attempted between non-matching template 119 that is associated with diagnostic/treatment device 118 and the primary interface template 95 that is associated with patient Anna 90.

Various implementation features may include providing an interface template associated with the particular patient, which interface template includes a customized interface configuration shaped for verifiable matching engagement with a complementary interface template associated with the health-related procedure. Some embodiments may provide one or more complementary interface templates associated with the health-related procedure. Some system features may provide multiple complementary interface templates that are each associated with a different product component, respectively. Another possible feature may provide one interface template associated with multiple product components.

Figure 4:
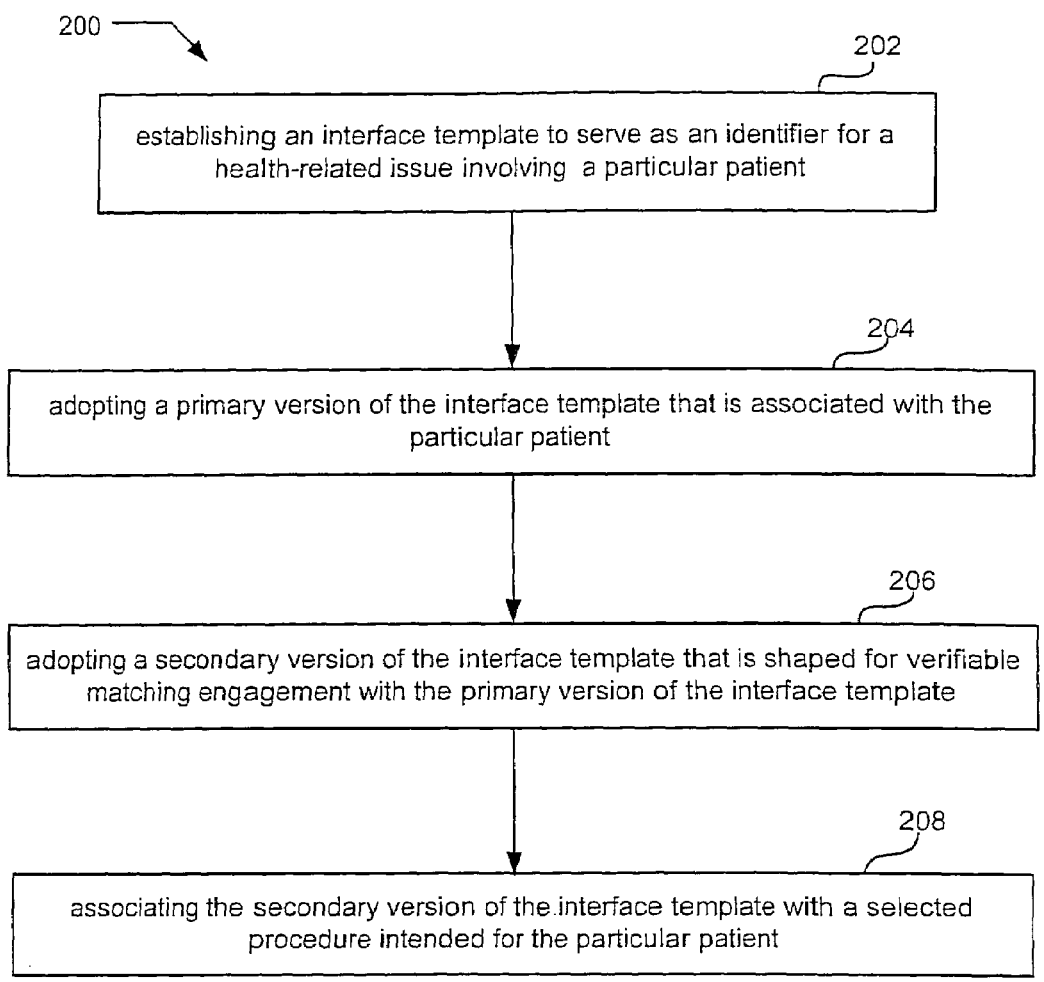
FIG. 4 is a high level flow chart for an exemplary process embodiment.

Referring to the high level flow chart of FIG. 4, an exemplary process embodiment 200 for patient verification includes establishing an interface template to serve as an identifier for a health-related issue involving a particular patient (block 202), adopting a primary version of the interface template that is associated with the particular patient (block 204), adopting a secondary version of the interface template that is shaped for verifiable matching engagement with the primary version of the interface template (block 206), and associating the secondary version of the interface template with a selected procedure intended for the particular patient (block 208).

Figure 5:
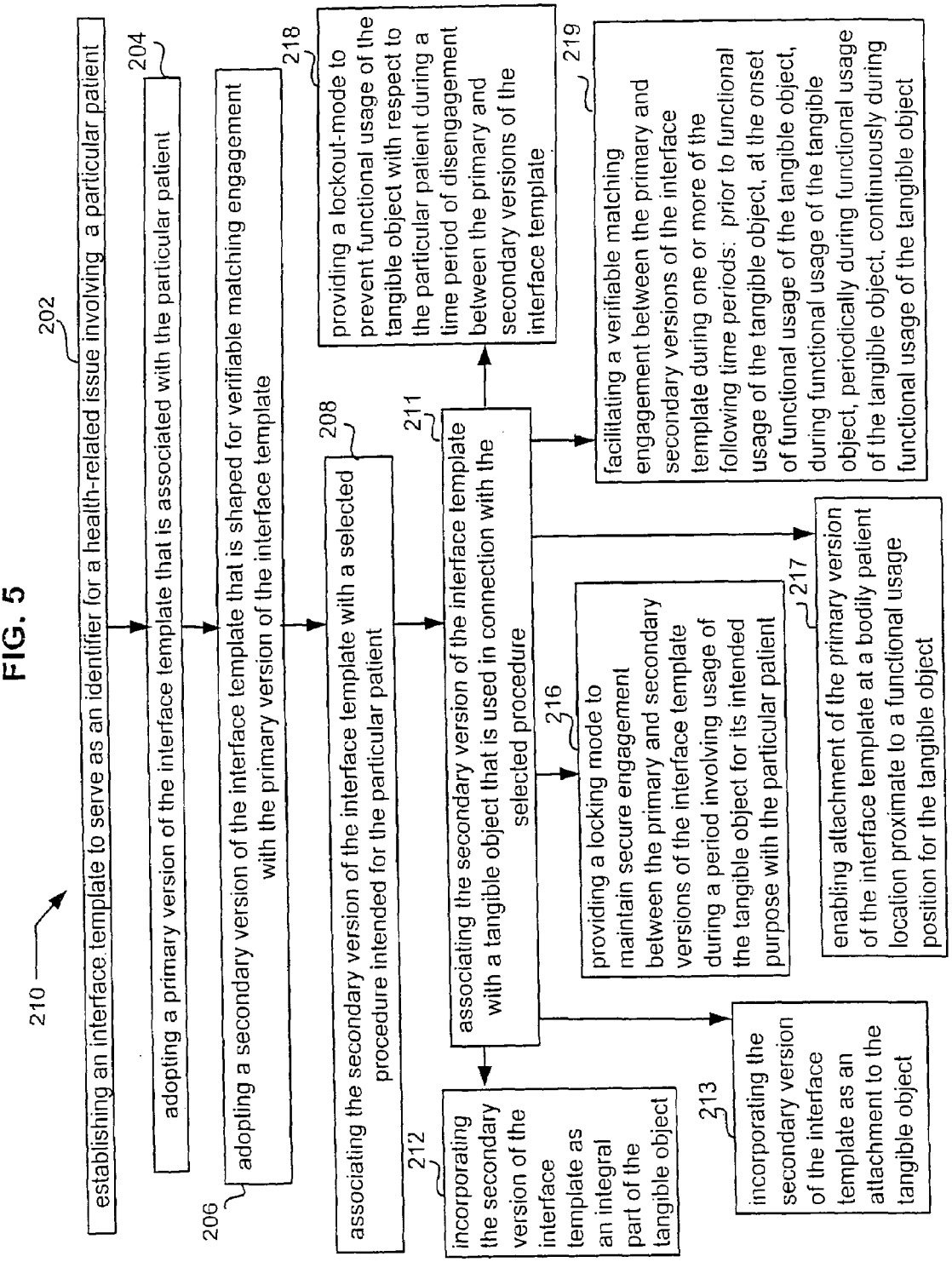
FIGS. 5-8 are flow charts showing more detailed aspects of various exemplary process embodiments.

The additional exemplary embodiment features 210 of FIG. 5 may include previously described process components 202, 204, 206, 908 in combination with associating the secondary version of the interface template with a tangible object that is used in connection with the selected procedure (block 211). Additional possible aspects may include incorporating the secondary version of the interface template as an integral part of the tangible object (block 212), and incorporating the secondary version of the interface template as an attachment to the tangible object (block 213).

Further possible features may include providing a locking mode to maintain secure engagement between the primary and secondary versions of the interface template during a period involving usage of the tangible object for its intended purpose with the particular patient (block 216), and enabling attachment of the primary version of the interface template at a bodily patient location proximate to a functional usage position for the tangible object (block 217).

FIG. 5 also discloses additional exemplary features including providing a lockout-mode to prevent functional usage of the tangible object with respect to the particular patient during a time period of disengagement between the primary and secondary versions of the interface template (block 218), and facilitating a verifiable matching engagement between the primary and secondary versions of the interface template during one or more of the following time periods: prior to functional usage of the tangible object, at the onset of functional usage of the tangible object, during functional usage of the tangible object, periodically during functional usage of the tangible object, continuously during functional usage of the tangible object (block 219).

Figure 6:
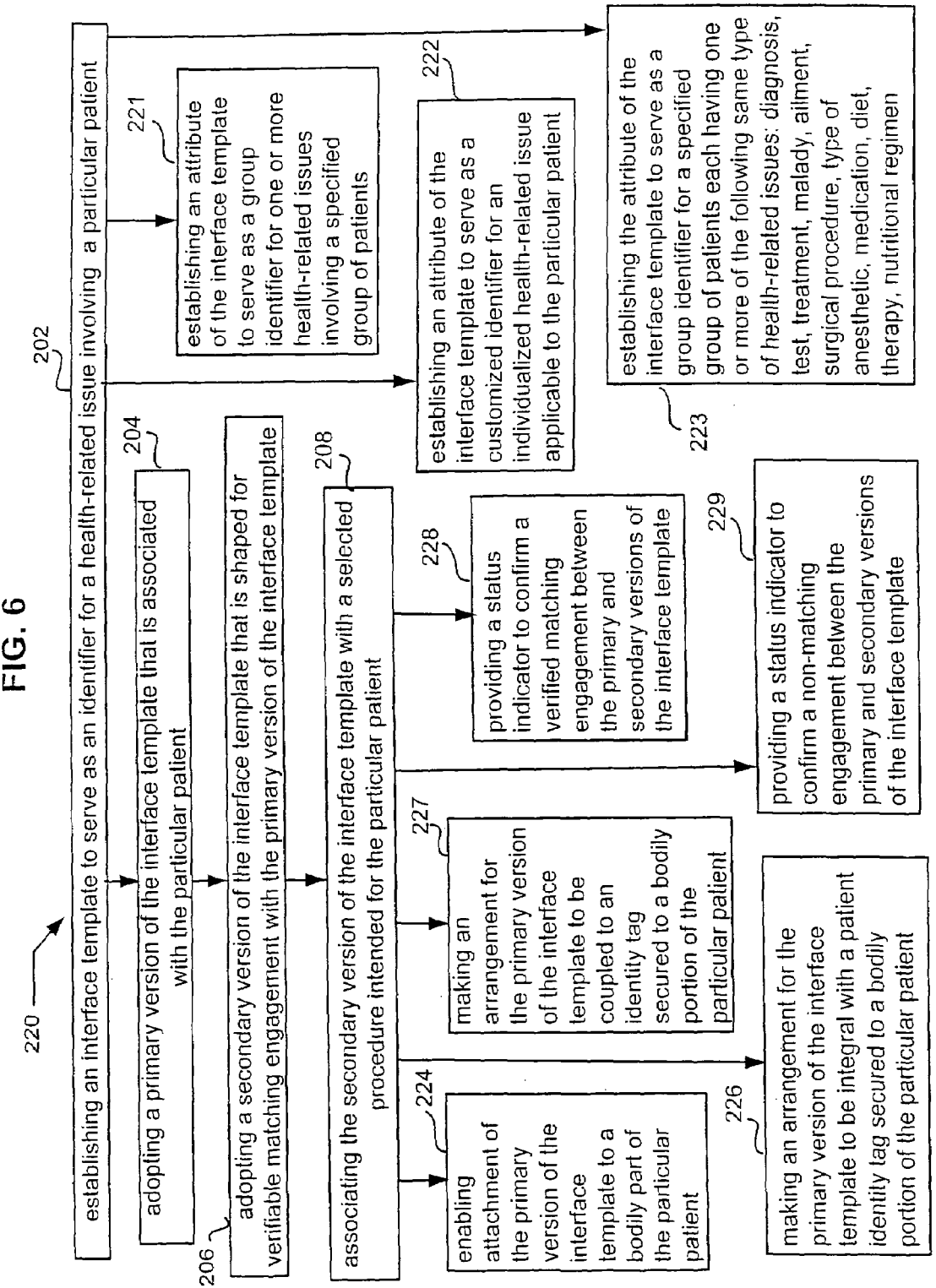

Referring to the exemplary embodiments 220 of FIG. 6, previously disclosed process components 202, 204, 206, 208 may be combined with other features relating to the primary version of the interface template. For example, possible aspects may include enabling attachment of the primary version of the interface template to a bodily part of the particular patient (block 224), making an arrangement for the primary version of the interface template to be integral with a patient identity tag secured to a bodily portion of the particular patient (block 226), and making an arrangement for the primary version of the interface template to be coupled to an identity tag secured to a bodily portion of the particular patient (block 227).

Other exemplary features may include providing a status indicator with an "ok" type of alert to indicate a verified matching engagement between the primary and secondary versions of the interface template (block 228), and providing a status indicator with a "warning" type of alert to indicate a non-matching engagement between the primary and secondary versions of the interface template (block 229).

Further possible implementation features shown in FIG. 6 may include establishing an attribute of the interface template to serve as a group identifier for one or more health-related issues involving a specified group of patients, (block 221), and establishing the attribute of the interface template to serve as a group identifier for a specified group of patients each having one or more of the following same type of health-related issues: diagnosis, test, treatment, malady, ailment, surgical procedure, type of anesthetic, medication, diet, therapy, and nutritional regimen (block 223), Another exemplary aspect may include establishing an attribute of the interface template to serve as a customized identifier for an individualized health-related issue applicable to the particular patient (block 222).

Figure 7:
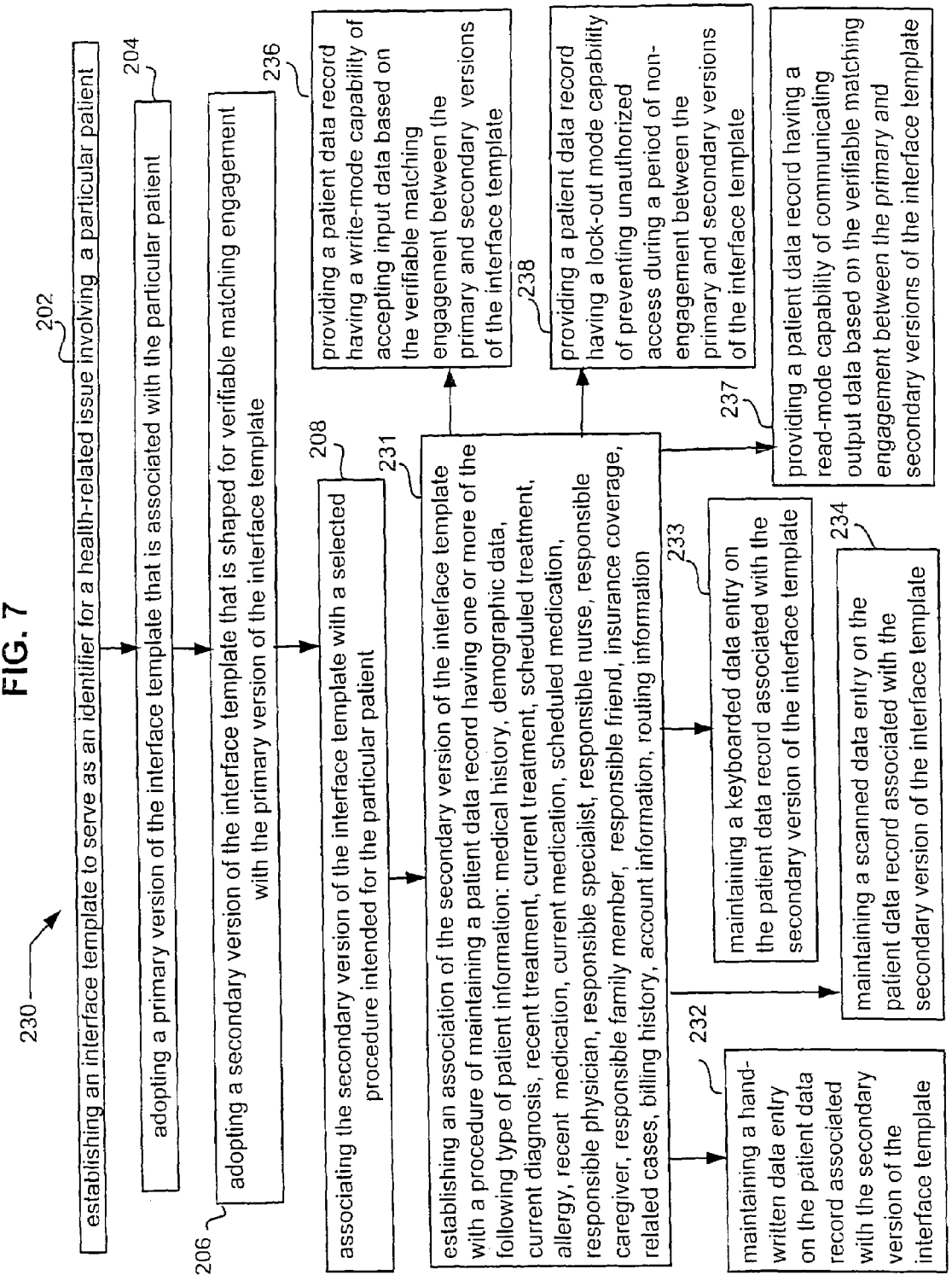

The exemplary process embodiments 230 shown in FIG. 7 may include previously described components 202, 204, 206, 208 along with establishing an association of the secondary version of the interface template with a procedure of maintaining a patient data record having one or more of the following type of patient information: medical history, demographic data, current diagnosis, recent treatment, current treatment, scheduled treatment, allergy, recent medication, current medication, scheduled medication, responsible physician, responsible specialist, responsible nurse, responsible caregiver, responsible family member, responsible friend, insurance coverage, related cases, billing history, account information, and routing information (block 231).

Further illustrated aspects that are possible include maintaining various types of data entries on the patient data record associated with the secondary version of the interface template, including a hand-written data entry (block 232), a keyboarded data entry (block 233), and a scanned data entry (block 234).

Further possible implementation features regarding the patient data record may include providing a patient data record having a write-mode capability of accepting input data based on the verifiable matching engagement between the primary and secondary versions of the interface template (block 236), and providing a patient data record having a read-mode capability of communicating output data based on the verifiable matching engagement between the primary and secondary versions of the interface template (block 237).

Another possible implementation feature may include providing a patient data record having a lock-out mode capability of preventing unauthorized access during a period of non-engagement between the primary and secondary versions of the interface template (block 238).

Figure 8:
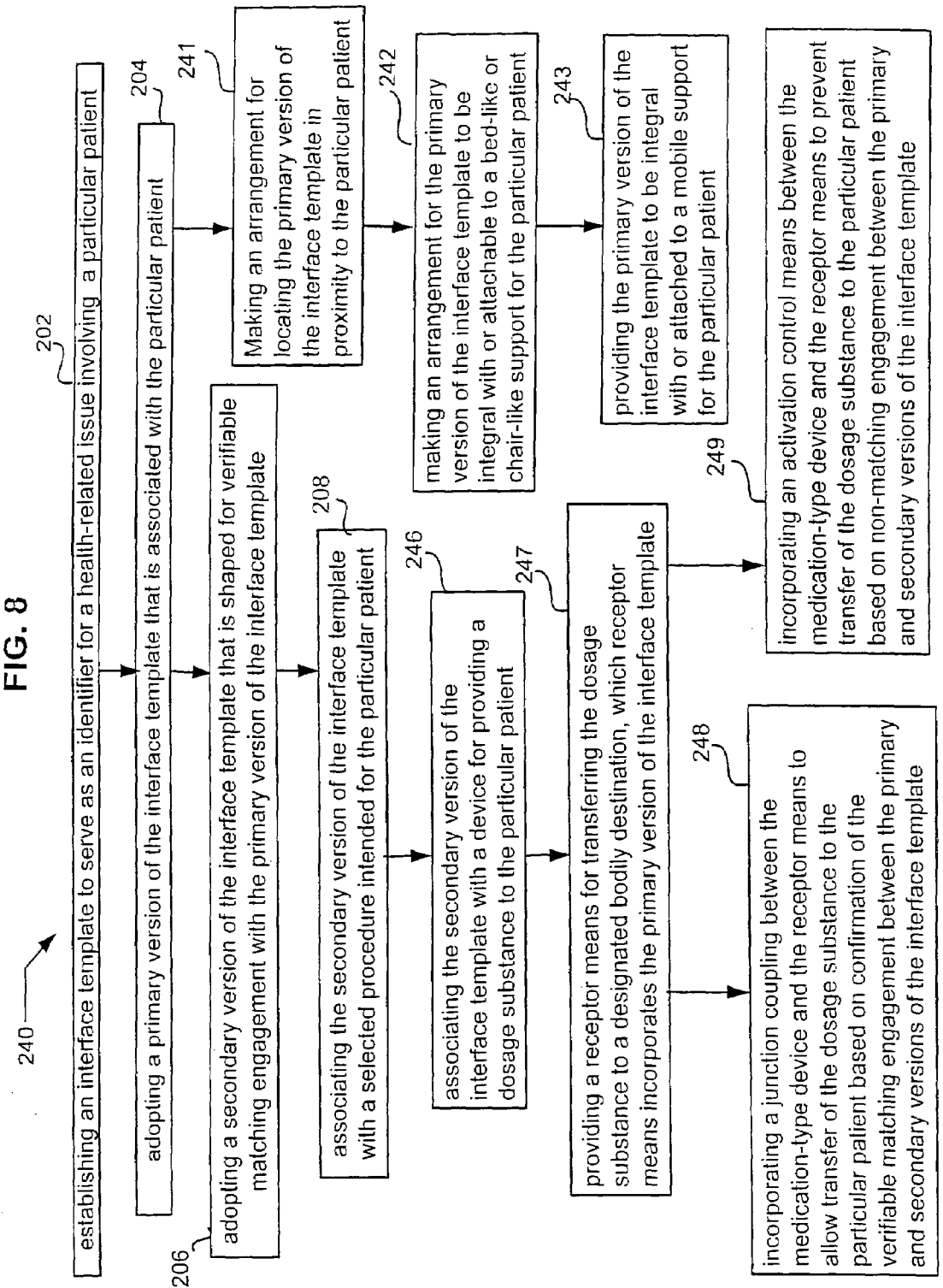

The detailed exemplary embodiment features 240 illustrated in FIG. 8 include previously described process components 202, 204, 206, 208 in combination with making an arrangement for locating the primary version of the interface template in proximity to the particular patient (block 241). Other possible aspects may include making an arrangement for the primary version of the interface template to be integral with or attachable to a bed-like or chair-like support for the particular patient (block 242). In some instances an exemplary embodiment feature may include providing the primary version of the interface template to be integral with or attached to a mobile support for the particular patient (block 243).

Other possible aspects shown in FIG. 8 include associating the secondary version of the interface template with a device for providing a dosage substance to the particular patient (block 246), providing a receptor means for transferring the dosage substance to a designated bodily destination, which receptor means incorporates the primary version of the interface template (block 247), and incorporating a junction coupling between the medication-type device and the receptor means to allow transfer of the dosage substance to the particular patient based on confirmation of the verifiable matching engagement between the primary and secondary versions of the interface template (block 248).

A further exemplary aspect may include incorporating an activation control means between the medication-type device and the receptor means to prevent transfer of the dosage substance to the particular patient based on non-matching engagement between the primary and secondary versions of the interface template (block 249).

Figure 9:
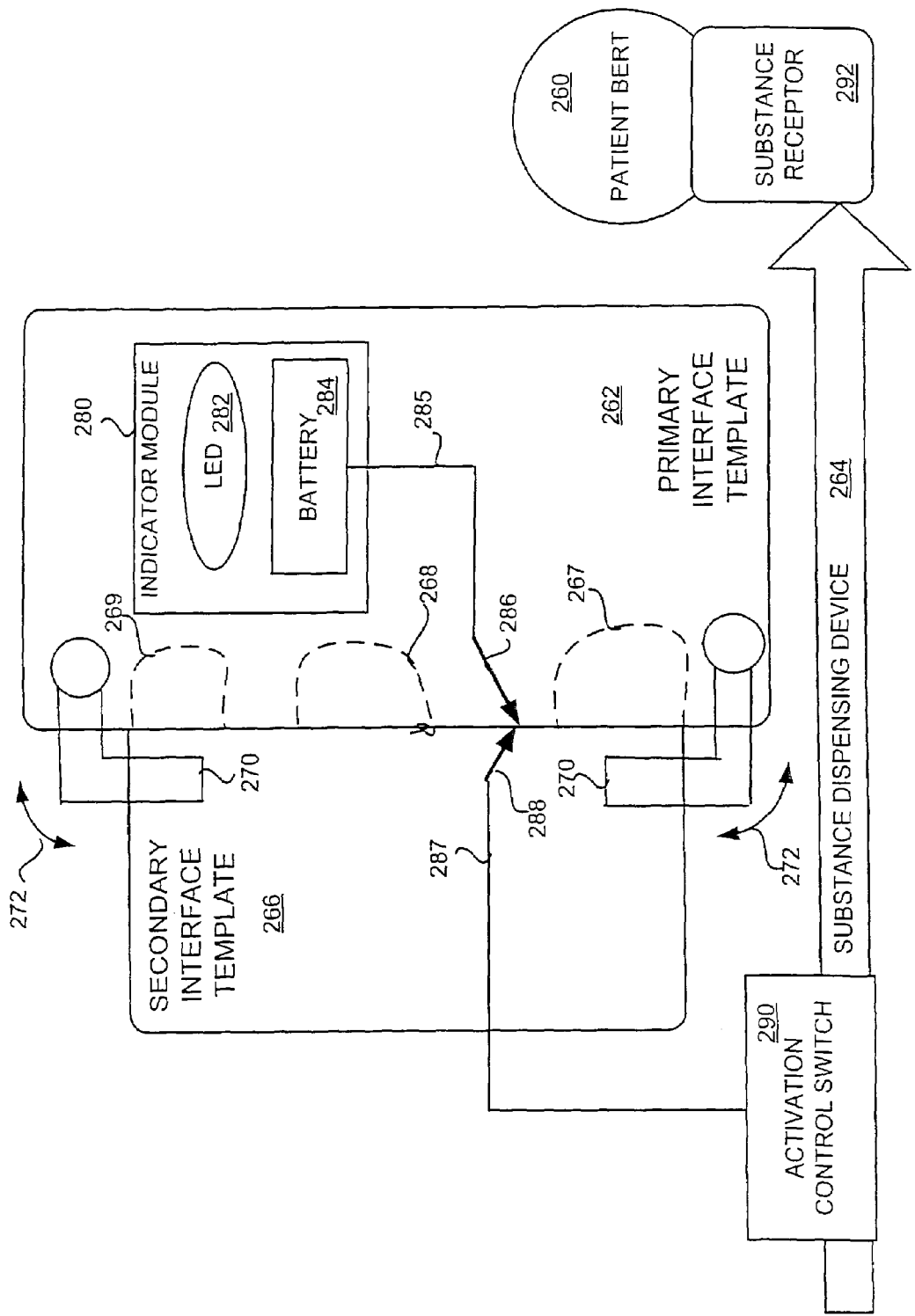
FIG. 9 is a schematic block diagram showing additional interface template embodiments.

The schematic block diagram of FIG. 9 illustrates an exemplary embodiment of a primary interface template 262 associated with patient Bert 260, and a matching secondary interface template 266 associated with substance dispensing device 264. The primary interface template 262 may include an indicator module 280 having a power source such as battery 284 and a status indicator such as light emitting diode (LED) 282. The primary interface template may also include a latching device such as pivotally mounted arms 270 that move back and forth (see arrows 272) between an unlatched position (with the primary interface template 262 and secondary interface template 266 disengaged—not shown) to a latched position with the primary interface template 262 and secondary interface template 266 in verifiable matching engagement (shown in FIG. 9).

Numerous types of matching interface shapes (e.g., pattern, projection, recess, matrix, contour, etc.) are possible for implementing a satisfactory matching engagement. In that regard, the illustrated version of the secondary interface template includes exemplary protrusions 267, 268, 269 (shown in phantom) that are shaped to form a customized pattern matching a complementary corresponding pattern (not shown) on the primary interface template 262.

A signal status line 285 connects battery 284 with a first conductive contact 286 on a surface portion of primary interface template 262. When full matching interface engagement occurs, a second conductive contact 288 is brought into adjacent relationship with the first conductive contact 286 to provide a closed circuit connection that establishes verification of a predetermined correct match-up between the substance dispensing device 264 and the intended recipient patient (or group of patients). Such verification may be confirmed by illumination of LED 282. Alternatively non-illumination of LED 282 is an indicator of non-engagement with the primary interface template 262.

Other functional consequences of such verified engagement may include a data entry provided to a patient data record (see patient data record 97 on FIG. 3), and transmission of a template engagement signal via status line 287 to activation control switch 290. Responsive to such template engagement signal, the activation control switch 290 serves as a junction coupling to enable delivery of a substance dosage via the substance dispensing device 264 to a substance receptor 292 for patient Bert 260. In the absence of such a template engagement signal, the activation control switch 290 remains closed to prevent delivery of any dosage through the substance dispensing device 264.

It will be understood that system embodiment features disclosed herein may be used with product components that include a device for dispensing a substance dosage for external administration to the particular patient, which device is associated with the interface template. In some instances the product components may include a device for dispensing a substance dosage for internal administration to the particular patient, which device is associated with the interface template.

Some embodiments may be implemented in a patient identification system for health-related procedures intended to be rendered to a specified group of patients having a same or similar type of health-related issue. An exemplary interface template may be associated with one or more product components, which interface template includes a customized interface configuration shaped for verifiable matching engagement with a complementary interface template associated with one or more of the patients in the specified group.

A possible group patient implementation aspect may provide a complementary interface template having a first attribute interface that includes a individualized ID configuration to serve as a customized identifier for a particular patient in the specified group, and also having a second attribute interface that includes a generic-type ID configuration to serve as an identifier for the specified group.

Another possible group aspect may provide a system having a complementary interface template that includes an attribute interface configuration to serve as an identifier associated with said health-related procedure.

It will be understood by those skilled in the art that the various components and elements disclosed in the block diagrams herein as well as the various steps and sub-steps disclosed in the flow charts herein may be incorporated together in different claimed combinations in order to enhance possible benefits and advantages.

It is to be further understood that various aspects of the methods and processes disclosed in FIG. 4-8 can be incorporated in one or more different types of computer program products with a carrier medium having program instructions encoded thereon. Some exemplary computer program products may be implemented in storage carrier media having program instructions encoded thereon. In some instances exemplary computer program products may be implemented in communication signal carrier media having program instructions encoded thereon.

The exemplary system, apparatus, and computer program product embodiments disclosed herein including FIGS. 1-3 and FIG. 9 along with other components, devices, know-how, skill and techniques that are known in the art have the capability of implementing and practicing the methods and processes shown in FIGS. 4-8. However it is to be further understood by those skilled in the art that other systems, apparatus and technology may be used to implement and practice such methods and processes. Those skilled in the art will also recognize that the various aspects of the embodiments for methods, processes, products, and systems as described herein can be implemented individually and/or collectively by a wide range of hardware, software, firmware, or any combination thereof.

Exemplary embodiments disclosed herein provide a verification technique that facilitates administration of a health-related procedure to an intended recipient patient or group of patients. An interface template may be configured to establish verifiable matching engagement between the patient and various types of objects used to administer the health-related procedure.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost versus efficiency tradeoffs. Those having skill in the art will appreciate that there are various vehicles by which processes and/or systems and/or other technologies described herein can be effected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle may be deployed and the specific concerns (e.g., speed, flexibility, or predictability) of the implementer, any of which may vary. Those skilled in the art will recognize that optical aspects of implementations will require optically-oriented hardware, software, and or firmware.

The foregoing detailed description has set forth various embodiments of the devices and/or processes via the use of block diagrams, flow diagrams, operation diagrams, flowcharts, illustrations, and/or examples. Insofar as such block diagrams, operation diagrams, flowcharts, illustrations, and/or examples contain one or more functions and/or operations, it will be understood by those within the art that each function and/or operation within such block diagrams, operation diagrams, flowcharts, illustrations, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

The herein described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components.

As a further definition of "open" terms in the present specification and claims, it will be understood that usage of a language construction "A or B" is generally interpreted as a non-exclusive "open term" meaning: A alone, B alone, A and B together.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A system comprising:
   circuitry configured for identifying at least one instance of engagement involving at least one patient interface template having identifying surface indicia;
   circuitry configured for at least partially enabling at least one health-related component based at least partly on the at least one instance of engagement involving at least one patient interface template having identifying surface indicia; and
   circuitry configured for communicating data for incorporation with at least one patient data record based at least partly on the at least one instance of engagement involving at least one patient interface template having identifying surface indicia.

2. The system of claim 1, wherein the circuitry configured for identifying at least one instance of engagement involving at least one patient interface template having identifying surface indicia comprises:
   circuitry configured for identifying at least one instance of engagement involving at least one patient interface template having one or more redundant identifying surface indicia.

3. The system of claim 1, wherein the circuitry configured for identifying at least one instance of engagement involving at least one patient interface template having identifying surface indicia comprises:
   circuitry configured for identifying at least one instance of engagement between at least one patient interface template having identifying surface indicia and at least one interface template associated with the at least one health-related component.

4. The system of claim 1, wherein the circuitry configured for identifying at least one instance of engagement involving at least one patient interface template having identifying surface indicia comprises:
   circuitry configured for identifying from one or more signals at least one instance of engagement involving at least one patient interface template having identifying surface indicia.

5. The system of claim 1, wherein the circuitry configured for identifying at least one instance of engagement involving at least one patient interface template having identifying surface indicia comprises:

circuitry configured for identifying at least one instance of physical engagement involving at least one patient interface template having identifying surface indicia.

6. The system of claim 1, wherein the circuitry configured for identifying at least one instance of engagement involving at least one patient interface template having identifying surface indicia comprises:
   circuitry configured for identifying at least one instance of complementary engagement involving at least one patient interface template having identifying surface indicia.

7. The system of claim 1, wherein the circuitry configured for identifying at least one instance of engagement involving at least one patient interface template having identifying surface indicia comprises:
   circuitry configured for identifying at least one instance of engagement between at least one patient interface template having identifying surface indicia and at least one other template.

8. The system of claim 1, wherein the circuitry configured for identifying at least one instance of engagement involving at least one patient interface template having identifying surface indicia comprises:
   circuitry configured for identifying at least one instance of engagement involving at least one patient interface template having identifying surface indicia composed of one or more geometric shapes.

9. The system of claim 1, wherein the circuitry configured for identifying at least one instance of engagement involving at least one patient interface template having identifying surface indicia comprises:
   circuitry configured for identifying at least one instance of engagement involving at least one patient interface template having identifying surface indicia composed of two or more geometric shapes.

10. The system of claim 1, wherein the circuitry configured for identifying at least one instance of engagement involving at least one patient interface template having identifying surface indicia comprises:
    circuitry configured for identifying at least one instance of engagement involving at least one patient interface template having identifying surface indicia formed from one or more physical protrusions and/or recesses.

11. The system of claim 1, wherein the circuitry configured for identifying at least one instance of engagement involving at least one patient interface template having identifying surface indicia comprises:
    circuitry configured for identifying at least one instance of engagement involving at least one patient interface template having identifying surface indicia composed of one or more patterns.

12. The system of claim 1, wherein the circuitry configured for identifying at least one instance of engagement involving at least one patient interface template having identifying surface indicia comprises:
    circuitry configured for identifying at least one instance of engagement involving at least one patient interface template having identifying surface indicia composed of one or more lines.

13. The system of claim 1, wherein the circuitry configured for identifying at least one instance of engagement involving at least one patient interface template having identifying surface indicia comprises:
    circuitry configured for identifying at least one instance of engagement involving at least one patient interface template having patient identifying surface indicia.

14. The system of claim 1, wherein the circuitry configured for identifying at least one instance of engagement involving at least one patient interface template having identifying surface indicia comprises:
    circuitry configured for identifying at least one instance of engagement involving at least one patient interface template having issue identifying surface indicia.

15. The system of claim 1, wherein the circuitry configured for identifying at least one instance of engagement involving at least one patient interface template having identifying surface indicia comprises:
    circuitry configured for identifying at least one instance of engagement involving at least one patient interface template having group identifying surface indicia.

16. The system of claim 1, wherein the circuitry configured for identifying at least one instance of engagement involving at least one patient interface template having identifying surface indicia comprises:
    circuitry configured for identifying at least one instance of engagement involving at least one patient interface template having procedure identifying surface indicia.

17. The system of claim 1, wherein the circuitry configured for at least partially enabling at least one health-related component based at least partly on the at least one instance of engagement involving at least one patient interface template having identifying surface indicia comprises:
    circuitry configured for at least partially enabling at least one treatment device based at least partly on the at least one instance of engagement involving at least one patient interface template having identifying surface indicia.

18. The system of claim 1, wherein the circuitry configured for at least partially enabling at least one health-related component based at least partly on the at least one instance of engagement involving at least one patient interface template having identifying surface indicia comprises:
    circuitry configured for at least partially enabling at least one testing device based at least partly on the at least one instance of engagement involving at least one patient interface template having identifying surface indicia.

19. The system of claim 1, wherein the circuitry configured for at least partially enabling at least one health-related component based at least partly on the at least one instance of engagement involving at least one patient interface template having identifying surface indicia comprises:
    circuitry configured for at least partially enabling at least one monitoring device based at least partly on the at least one instance of engagement involving at least one patient interface template having identifying surface indicia.

20. The system of claim 1, wherein the circuitry configured for at least partially enabling at least one health-related component based at least partly on the at least one instance of engagement involving at least one patient interface template having identifying surface indicia comprises:
    circuitry configured for at least partially enabling at least one administration device based at least partly on the at least one instance of engagement involving at least one patient interface template having identifying surface indicia.

21. The system of claim 1, wherein the circuitry configured for at least partially enabling at least one health-related component based at least partly on the at least one instance of engagement involving at least one patient interface template having identifying surface indicia comprises:
    circuitry configured for at least partially enabling access to at least one patient data record based at least partly on the at least one instance of engagement involving at least one patient interface template having identifying surface indicia.

22. The system of claim 1, wherein the circuitry configured for communicating data for incorporation with at least one patient data record based at least partly on the at least one instance of engagement involving at least one patient interface template having identifying surface indicia comprises:
 circuitry configured for incorporating data with at least one patient data record based at least partly on the at least one instance of engagement involving at least one patient interface template having identifying surface indicia.

23. The system of claim 1, wherein the circuitry configured for communicating data for incorporation with at least one patient data record based at least partly on the at least one instance of engagement involving at least one patient interface template having identifying surface indicia comprises:
 circuitry configured for communicating data for incorporation with at least one patient data record responsive to the at least one instance of engagement involving at least one patient interface template having identifying surface indicia.

24. A system comprising:
 at least one article of manufacture bearing one or more instructions for facilitating operations including
  identifying at least one instance of engagement involving at least one patient interface template having identifying surface indicia;
  at least partially enabling at least one health-related component based at least partly on the at least one instance of engagement involving at least one patient interface template having identifying surface indicia; and
  communicating data for incorporation with at least one patient data record based at least partly on the at least one instance of engagement involving at least one patient interface template having identifying surface indicia.

25. A method at least partially implemented using one or more processing components comprising:
 identifying at least one instance of engagement involving at least one patient interface template having identifying surface indicia;
 at least partially enabling at least one health-related component based at least partly on the at least one instance of engagement involving at least one patient interface template having identifying surface indicia; and
 communicating data for incorporation with at least one patient data record based at least partly on the at least one instance of engagement involving at least one patient interface template having identifying surface indicia.

* * * * *